United States Patent
Gouripeddi et al.

(10) Patent No.: US 10,902,840 B2
(45) Date of Patent: Jan. 26, 2021

(54) METHOD AND SYSTEM FOR THOUGHT-TO-SPEECH

(71) Applicant: SAI Society for Advanced Scientific Research, Bangalore (IN)

(72) Inventors: Prabhakara Rao Venkata Gouripeddi, Bangalore (IN); Hanumantha Rao Naidu Devireddy, Bangalore (IN)

(73) Assignee: SAI SOCIETY FOR ADVANCED SCIENTIFIC RESEARCH, Bangalore (IN)

( * ) Notice: Subject to any disclaimer, the term of this patent is extended or adjusted under 35 U.S.C. 154(b) by 17 days.

(21) Appl. No.: 15/993,322

(22) Filed: May 30, 2018

(65) Prior Publication Data
US 2018/0350342 A1 Dec. 6, 2018

(30) Foreign Application Priority Data
May 31, 2017 (IN) .............................. 201741019061

(51) Int. Cl.
| | |
|---|---|
| *G10L 13/00* | (2006.01) |
| *G10L 13/027* | (2013.01) |
| *A61B 5/00* | (2006.01) |
| *G06F 3/01* | (2006.01) |
| *A61B 5/16* | (2006.01) |
| *G10L 15/24* | (2013.01) |

(52) U.S. Cl.
CPC .......... *G10L 13/027* (2013.01); *A61B 5/0064* (2013.01); *A61B 5/165* (2013.01); *A61B 5/4803* (2013.01); *A61B 5/4836* (2013.01); *G06F 3/015* (2013.01); *G10L 15/24* (2013.01)

(58) Field of Classification Search
USPC ................................................. 704/231–275
See application file for complete search history.

(56) References Cited

U.S. PATENT DOCUMENTS

| | | | | |
|---|---|---|---|---|
| 2007/0083097 | A1* | 4/2007 | Fujiwara | A61B 5/742 600/407 |
| 2011/0319784 | A1* | 12/2011 | Nakagawa | A61B 5/0476 600/544 |
| 2014/0163960 | A1* | 6/2014 | Dimitriadis | G10L 25/63 704/9 |

(Continued)

OTHER PUBLICATIONS

Van Wijk et al. "Anatomic Characterization of human ultra-weak photon emission with a moveable photomultiplier and CCD imaging". Journal of Photochemistry and Photobiology B: Biology 83 (2006) 69-76 (Year: 2006).*

*Primary Examiner* — Jesse S Pullias
(74) *Attorney, Agent, or Firm* — Ference & Associates LLC

(57) ABSTRACT

One embodiment provides a method, including: collecting, at an information handling device, at least one signal received from a living object, in response to an event associated with the living object, wherein the living object is in a communicative state with a person talking to the living object; extracting, using a processor, a set of predetermined features from the signal collected; and determining, responsive to extracting, an intent associated with the living object in response to the event posed to the living object from the strength of the signal. Other embodiments are disclosed and described.

18 Claims, 6 Drawing Sheets

300

(56) References Cited

U.S. PATENT DOCUMENTS

| 2015/0221304 A1* | 8/2015 | Stewart | G10L 15/18 |
| | | | 704/235 |
| 2015/0297126 A1* | 10/2015 | Atsumori | A61B 5/7475 |
| | | | 600/328 |
| 2016/0071517 A1* | 3/2016 | Beaver | G06F 17/279 |
| | | | 704/9 |

* cited by examiner

METHOD AND SYSTEM FOR THOUGHT-TO-SPEECH

CROSS REFERENCE TO RELATED APPLICATIONS

This application claims priority to Patent Application Serial No. 201741019061 filed in India on May 31, 2017, and entitled "METHOD AND SYSTEM FOR THOUGHT-TO-SPEECH," the contents of which are incorporated by reference herein.

BACKGROUND

Currently, it is known that, Amyotrophic lateral sclerosis (ALS) is a neurodegenerative disease of the nervous system that may destroy parts of a central nervous system (CNS), which is responsible for movement, but without influencing senses, cognitive abilities and intellect. Usually, people, who suffer from ALS may gradually lose control over their own body and within a few months to a few years reach a state where they have no ability to communicate with their environment. Typically, there may be several situations that can lead an individual to a state wherein he/she may be trapped within herself/himself and unable to communicate with the world in a natural way. Generally, like ALS, diseases such as brainstem stroke, brain or spinal cord injury, cerebral palsy, muscular dystrophies, multiple sclerosis, chronic polyneuritis (Guillan-Barré syndrome) may result in impairing the neural pathways that control muscles or impair the muscles themselves. For patients having residual voluntary control over few muscles, such as eye movement, eye blinks, or twitches of the lip are generally referred to as locked-in state (LIS) patient, it may become an important aspect to measure a response from such patients/humans.

BRIEF SUMMARY

In summary, one aspect of the invention provides a method, comprising: collecting, at an information handling device, at least one signal received from a living object, in response to an event associated with the living object, wherein the living object is in a communicative state with a person talking to the living object; extracting, using a processor, a set of pre-determined features from the signal collected; and determining, responsive to extracting, an intent associated with the living object in response to the event posed to the living object from the strength of the signal.

A further aspect of the invention provides an information handling device, comprising: a processor; a memory device that stores instructions executable by the processor to: collect, at an information handling device, at least one signal received from a living object, in response to an event associated with the living object, wherein the living object is in a communicative state with a person talking to the living object; extract, using a processor, a set of pre-determined features from the signal collected; and determine, responsive to extracting, an intent associated with the living object in response to the event posed to the living object from the strength of the signal.

An additional aspect of the invention provides a product, comprising: a storage device that stores code, the code being executable by a processor and comprising: code that collects, at an information handling device, at least one signal received from a living object, in response to an event associated with the living object, wherein the living object is in a communicative state with a person talking to the living object; code that extracts, using a processor, a set of pre-determined features from the signal collected; and code that determines, responsive to extracting, an intent associated with the living object in response to the event posed to the living object from the strength of the signal.

For a better understanding of exemplary embodiments of the invention, together with other and further features and advantages thereof, reference is made to the following description, taken in conjunction with the accompanying drawings, and the scope of the claimed embodiments of the invention will be pointed out in the appended claims.

DETAILED DESCRIPTION

Figure 1:
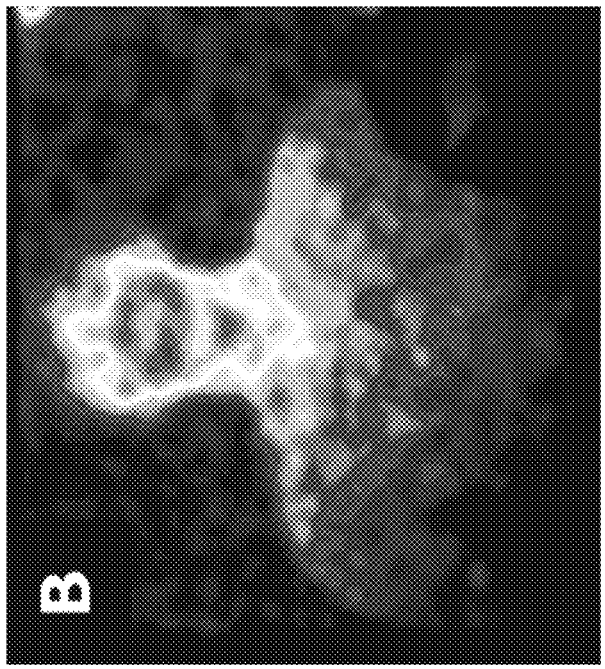
FIG. 1 illustrates an exemplary Image of the person under light illumination (A) on the left hand side and a corresponding Image of biophoton emission from the human body (B) on the right hand side.
Figure 1:
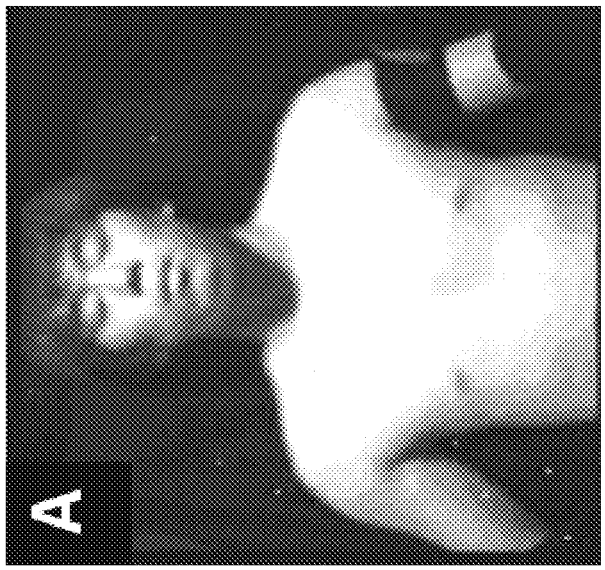

It will be readily understood that the components of the embodiments of the invention, as generally described and illustrated in the figures herein, may be arranged and designed in a wide variety of different configurations in addition to the described exemplary embodiments. Thus, the following more detailed description of the embodiments of the invention, as represented in the figures, is not intended to limit the scope of the embodiments of the invention, as claimed, but is merely representative of exemplary embodiments of the invention.

Reference throughout this specification to "one embodiment" or "an embodiment" (or the like) means that a particular feature, structure, or characteristic described in connection with the embodiment is included in at least one embodiment of the invention. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in at least one embodiment. In the following description, numerous specific details are provided to give a thorough understanding of embodiments of the invention. One skilled in the relevant art may well recognize, however, that embodiments of the invention can be practiced without at least one of the specific details thereof, or can be practiced with other methods, components, materials, et cetera. In other instances, well-known structures, materials, or operations are not shown or described in detail to avoid obscuring aspects of the invention.

The illustrated embodiments of the invention will be best understood by reference to the figures. The following description is intended only by way of example and simply illustrates certain selected exemplary embodiments of the invention as claimed herein. It should be noted that the flowchart and block diagrams in the figures illustrate the architecture, functionality, and operation of possible implementations of systems, apparatuses, methods and computer program products according to various embodiments of the invention. In this regard, each block in the flowchart or block diagrams may represent a module, segment, or portion of code, which comprises at least one executable instruction for implementing the specified logical function(s).

It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Hereinafter, various exemplary embodiments of the present disclosure will be described with reference to the accompanying drawings, where all of these drawings and description are only presented as exemplary embodiments. It is to be noted that based on the subsequent description, alternative embodiments may be conceived that may have a structure and method disclosed as herein, and such alternative embodiments may be used without departing from the principle of the disclosure as claimed in the present disclosure.

References in the specification to "one embodiment", "an embodiment", "a preferred embodiment" etc., indicate that the embodiment described may include a particular feature, structure, or characteristic, but every embodiment may not necessarily include the particular feature, structure, or characteristic. Moreover, such phrases are not necessarily referring to the same embodiment. It should also be understood that various terminology used herein is for the purpose of describing particular embodiments only and is not intended to be limiting the scope and spirit of this disclosure. As used herein, the singular forms "a", "an" and "the" may include the plural forms, unless the context clearly indicates otherwise. It will be further understood that the terms "comprises", "has" and "including" used herein, specify the presence of stated features, elements, and/or components etc., but do not preclude the presence of one or more other features, elements, components and/or combinations thereof. For example, the term "multiple" used here indicates "two or more"; the term "and/or" used here may comprise any or all combinations of one or more of the items listed in parallel. Definitions of other terms will be specifically provided in the following description. Furthermore, in the following description, some functions or structures well-known to those skilled in the art will be omitted in order not to obscure embodiments of the disclosure in the unnecessary details.

It may be appreciated that these exemplary embodiments are provided only for enabling those skilled in the art to better understand and then further implement the present disclosure, not intended to limit the scope of the present disclosure in any manner. Besides, in the drawings, for a purpose of illustration, optional steps, modules, and units may be illustrated in dotted-line blocks.

Embodiments of the present disclosure relates to a system, a computer program product, an article of manufacture and a method for measuring a status, which for example may be an emotional status or an intention, associated with a living object, for example a human being, by collecting at least one signal emitted/transmitted from a living object; extracting a set of pre-determined features from the signal collected; mapping the set of pre-determined features to a lookup table and/or a catalogue; and determining/deciphering a status associated with the living object from the mapping between the set of pre-determined features extracted and the lookup table and thereby determine the emotional status or the intention of the living object, wherein the living object is not able to communicate with other living objects in a normal manner.

Embodiments of the present disclosure are related to a system and/or an article of manufacture and/or a computer program product and/or a method for measuring a status associated with a living object. One embodiment may include collecting at least one signal emitted/transmitted from a living object. A further embodiment may include extracting a set of pre-determined features from the signal collected. A further embodiment may include mapping the set of pre-determined features to a lookup table and/or a catalogue. A further embodiment may include determining/deciphering a status associated with the living object from the mapping between the set of pre-determined features extracted and the lookup table. In a further exemplary embodiment the status associated with the living object may be at least one of an emotional status and/or an intention. In a further exemplary embodiment, the living object may be a human being. In a further embodiment, the living object may not be in a position to communicate with other living objects in a normal manner, for example the living object may be in a state of coma.

In a further embodiment, the signal emitted from the living object may include low intensity photons. In one exemplary embodiment, such low intensity photons may be biophotons. In a further embodiment, the low intensity biophotons may be emitted in response to the event occurring in the living object, the event occurring in response to an external stimulus. In a further embodiment, the external stimulus may be a question or a series of questions posed to the living object, to which the living object may respond by emitting the biophotons. In a further embodiment, the external stimulus may be a conversation with the living object, to which the living object may respond by emitting biophotons. In a further embodiment, these biophotons may be collected by a low intensity photon detector. In a further embodiment, the collected photon may be associated with a binary value such as YES or NO. In a further embodiment, the biophoton may be associated with a different type of answer associated with the question posed to the living object.

A further embodiment may include analyzing the low intensity photon (hereinafter interchangeably used with biophotons) that are emitted from the living object and collected using a low intensity photon detector. In a further embodiment, the pre-determined parameters collected from the biophoton may be compared with a lookup table and/or a catalogue that may include trained classifiers and/or data points, which may allow the user to decipher the emotional status and/or intention of the living object. In a further embodiment, the classifiers and/or the data points may establish a correlation with the set of pre-determined features extracted from the signal emitted from the living object and collected by the low intensity photon detector.

A further embodiment may include determining if the living object is in a cooperative state from the correlation established. In yet a further embodiment, if it may be determined that the living object is in the cooperative state, the embodiment may include posing a series of questions to the living object. In yet a further embodiment, after posing a question and/or a series of question to the living object, the embodiment may include deciphering the intent of the living object from the response received from the object, wherein the response received is a biophoton, and the response may be received to the question posed. In a further embodiment, the response may be a binary state of YES or NO. In a further embodiment, the question posed to the living object and the intent and/or emotional status deciphered from the living object may be fed to a speech based system, wherein the speech system is allowed to speak the question posed and the answer from the biophoton (biophoton signal), which is a YES or NO to the question, may also be output on the speech based system.

In one embodiment, biophoton emissions (BPEs), may be spontaneous non-thermal low intensity light emissions from every living cell, to build the thought-to-speech system. In a further embodiment, BPEs have been used in studies previously, especially in the context of diverse fields such as cancer research, noninvasive early medical diagnosis, food and water quality testing, chemical and electromagnetic contamination testing, cell communication, and various other applications in biotechnology. In a further embodiment, BPEs emitted due to activity which arise from emotions and/or intentions of a patient, offers the possibility to recognize underlying emotions and/or intentions of a person, which may be the key principle underlying whether the living object is responsive or not. In a further embodiment, these BPEs may arise from the human brain, fingers, palm, chest, forehead etc. In a further embodiment, the application of biophoton emission principles may be expected to significantly advance the state-of-the art in providing a convenient, noninvasive means of communication for locked-in individuals. In one embodiment, the emotional state and/or intention of an individual and/or human being and/or living object may be detected using the BPEs. In a further embodiment, an individual's response, in terms of binary state of YES or NO may be detected to a defined set of questions susing the BPEs.

FIG. 1 depicts the biophoton emission from human body. The left hand side of FIG. 1 labelled as A is an Image of the same person under light illumination as is well know in the art (include reference link here). The right hand side of FIG. 1 labelled as B is an Image of biophoton emission from the human body. In one embodiment, biophoton may be classified as a photon of non-thermal origin in the visible and ultraviolet spectrum emitted from a biological system. In a further embodiment, all living organisms, including humans, spontaneously emit ultra-weak photons, commonly known as biophotons. In a further embodiment, this low intensity glow cannot be seen by the naked eye, but can be measured by a detector, such as a photomulipliers, that amplify the weak signals several million time to enable the researcher to register it in the form of a diagram. In a further embodiment, as long as they live, cells and whole organisms give off a pulsating glow with a mean intensity of several up to a few thousand photons per second a per square centimeter, which in one embodiment may correspond to a candlelight seen from 15-mile distance.

Figure 2:
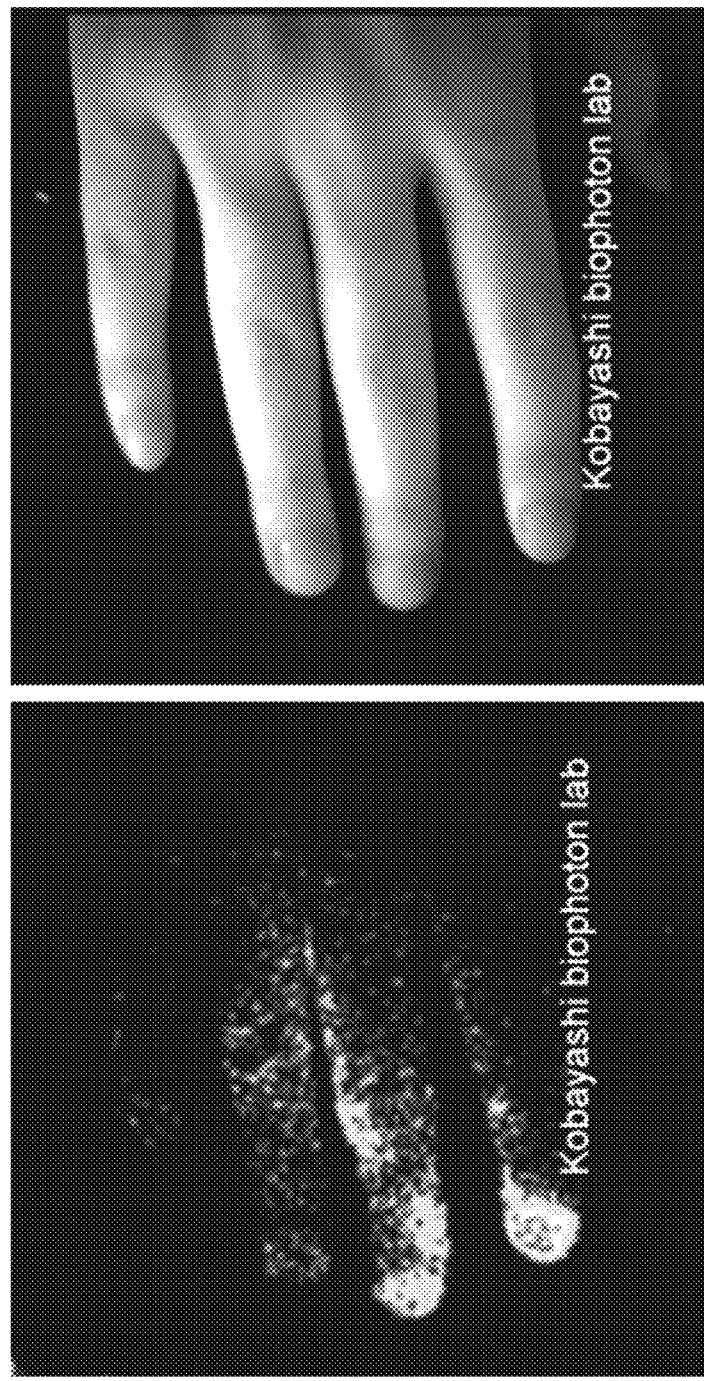
FIG. 2 illustrates an exemplary embodiment of biophoton emission imaging in accordance with the present disclosure.

FIG. 2 illustrates an exemplary embodiment of an image of biophoton emission imaging taken from Kobayashi biophoton lab, Sendai, Japan, which may be referenced as http://www.tohtech.ac.jp/~elecs/ca/labs/kobayashilab_hp/BiophotonGalleryE.html, The image on the left is an illustration of ultraweak photon emission from fingers, with the fingertip showing oxidative damage of the skin due to cigarette smoking of the person. The image on the right is under normal light illumination. In one embodiment, the glow may also be made visible by means of a CCD camera whose input of differences in brightness may be transformed by a computer into colors displayed on a video screen. In a further embodiment, because of its low intensity, the BPE may also be referred to as ultra-weak cell radiation, or ultra-weak bioluminescence or ultra-weak photon emissions.

In some embodiments, biophotons typically have a wavelength from 200 nm to 800 nm (0.2-0.8 µm). In some other embodiments, BPEs may be usually observed in a close UV range (from 300 nm to 400 nm) and visible optic range (from 0.38 µm to 0.75 µm) with frequencies ranging from 10-19 to 10-16 W/cm2 (with density approx. 1-1000 photons. cm-2. sec-1). In some other embodiments, BPEs light intensity may be much weaker than the one that may be seen in the perceptually visible and normal bioluminescence, but may be detectable above the background of thermal or infrared (0.74-2.5 µm) radiation emitted by tissues at their normal temperature. In some other embodiments, this type of light may not be radiated in a dispersed way as daylight, but may be dispersed quite coherently maintaining order in the flow oscillations, stability and continuity of a phase difference of an amplitude of the total wave. In an example embodiment, it might be both semi-periodic and coherent. In some other embodiments, it is typically known that coherence may be an ideal property of waves that enables stationary (i.e., temporally and spatially constant) interference. In yet some other embodiments, this may signify that biophotons in the light's beam vibrate simultaneously, like in a laser beam that may indicate on information characteristics of the signal.

In some embodiments, "delayed luminescence" may be connected with hyperbolic relaxation of biological objects that is a characteristic active response of coherent states. In some other embodiments, evidence has been found that biophoton light may have a high degree of coherence because of its photon count statistics, the spectral distribution, unstable decay behavior after exposure to light illumination, and its transparency through optically thick materials. In yet some other embodiments, BPE correlates strongly with all the life activities of organisms by which it is emitted, and therefore probably fulfills some biological function(s). In yet some other embodiments, unlike chemical bioluminescence, before death of an organism, its BPE intensity increases steeply, more than a hundred or a thousand fold, and then decreases down to zero at the moment of death. In some other embodiments, radiation increases during mitosis (cell division) and undergoes very characteristic changes during all phases of a cell cycle. In some other embodiments, it reacts very sensitively to all disturbances, external influences, and inner changes in the organism, and for this reason, its measurements can be used as reliable and sensitive indictor for such influences and changes. In some embodiments, it is well known that the human body is glimmering with light of intensity weaker than $\frac{1}{1000}$ times the sensitivity of naked eyes. In some other embodiments, using for example a sensitive charge-coupled device (CCD) camera with the ability to detect light at the level of a single photon, imaging the spontaneous photon emission from human bodies may be successful.

Figure 3:
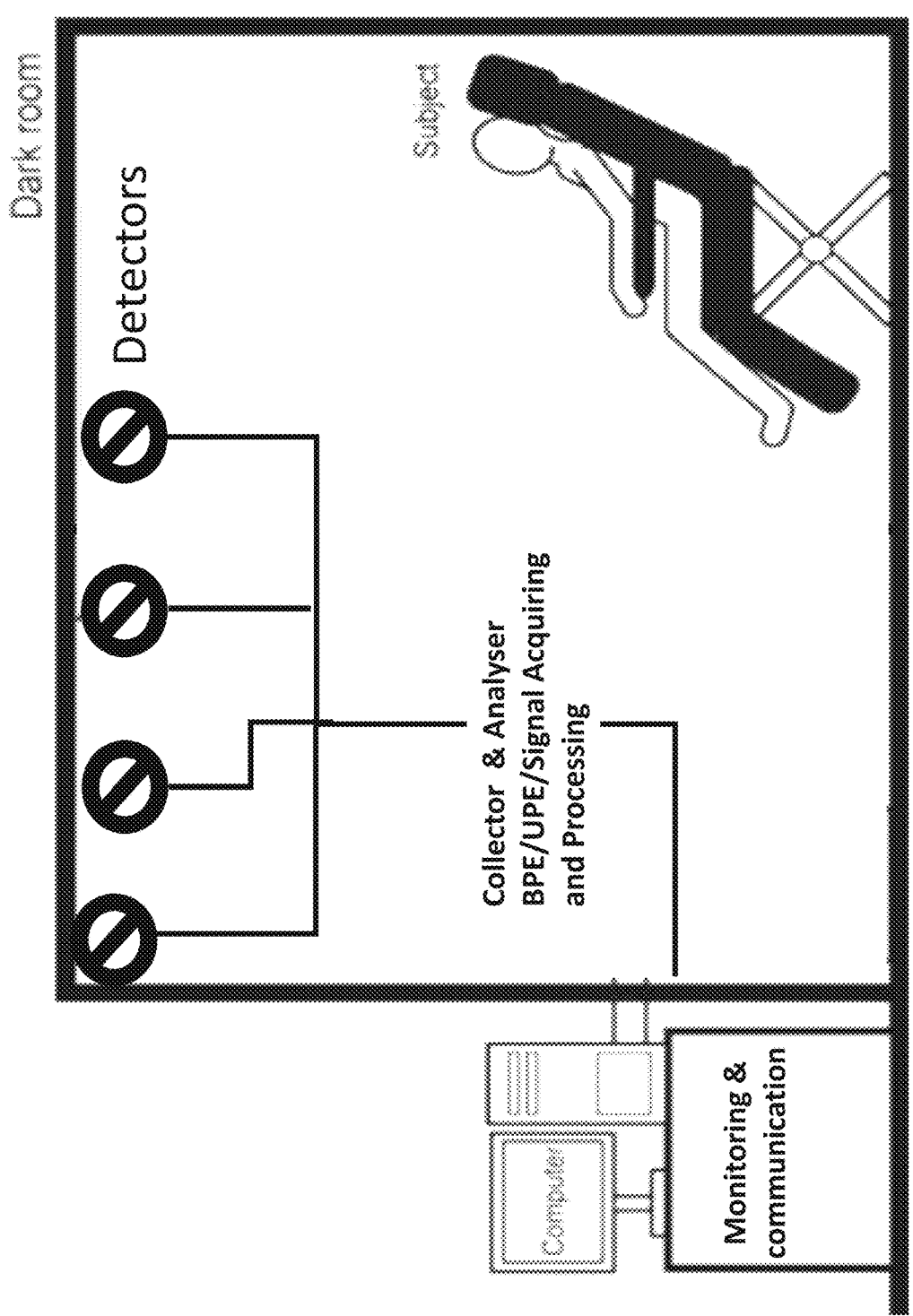
FIG. 3 is a schematic illustration of exemplary experimental setup used for capturing ultraweak photon emission from human body.

FIG. 3 is a schematic illustration of exemplary experimental setup used for capturing ultraweak photon emission from human body. The emission of all points on the body displayed a clear dependence on the various known biological rhythms (24 hours, weekly, monthly). Measurements on the symmetric points on both the sides of the body led to the tentative assumption that symmetric measurement values indicate healthy states while right-left asymmetric measurement value are an indication of disturbances. An interesting finding is that the changes in BPE after treatment were not only observed at the position of treatment, but also appeared at other places of the body. These nonlocal effects seem to demonstrate that the local BPE is an expression of a global biophoton field of the whole organism. As discussed previously, BPEs may be detected from various parts of the patient including the brain, palm, chest, fingers etc. by the detectors and consolidated for analysis and further study and interpretation of the patient.

FIG. 3 illustrates an of exemplary experimental setup used for capturing ultraweak photon emission from human body especially in the case of LIS and CLIS patients, which are typically performed in a dark room In one embodiment, these signals may be picked up by highly sensitive detectors even during daylight. The scope of such detectors does not fall within the purview of this embodiments of the present disclosure. A person (subject) sitting in typically placed in a dark room, which may be air conditioned such that the person is not subject to any uncomfortable situations such as sweating etc. At least one detector is placed in the room, which may be configured to monitor and capture the biophoton emissions from the person. In one embodiment, a plurality of detectors, for example extremely sensitive detectors, including at least one of a photodetector, CCD camera, infra-red camera or any other form of photon detecting device may be used to capture the biophoton emitted from the subject. Biophotons captured by the detector may be then sent to a collector and analyzing unit, which can analyses the biophotons. In one embodiment, the collector and analyzing unit may be a single unit. In one embodiment, the collector and analyzing unit may be outside the dark room to avoid interference from other objects. The unit is coupled to a counter to process the response and produce it to a text to speech system integrated into the computing system such that the output may be produced in spoken form. In a further embodiment, the collector and analyzing unit may be part of the computing system itself.

In one embodiment, the person is monitored by the detector which may be operated automatically or manually. In a further embodiment, signals detected by the detector may be processed by the signal processor, the signals are then analyzed and deciphered, and the deciphered signals may be recorded.

In some embodiments, it may be assumed that the human brain may generate higher densities of photons compared to other parts of the body. In some embodiments, recent experiments examined a relationship between BPE, visualization, as well as an intention, and suggest that imagining white light consistently produces an increase in photon emission from the right side of the head compared to both mundane thoughts and baseline conditions. In some other embodiments, measurements by a photomultiplier tube at distances of 15 cm from the head demonstrated significant increases in biophoton energies along the right side but not the left when subjects imagined white light in a dark environment. In some other embodiments, increased power density of $3 \times 10^{-11}$ W/m2, did not occur when the same subjects thought about mundane experiences. In some other embodiments, the calculated increased photon energy while imagining white light was equivalent to the involvement of action potentials from about 107 cerebral cortical neurons.

In some embodiments, cerebral BPE as a potential factor in non-local human-machine interaction was considered and subjects were instructed to employ intention to affect the direction of random number generation from a device located on their right side at 1 m distance. In some other embodiments, BPEs from the right hemisphere were recorded simultaneously. In some other embodiments, a significant increase ($3.5.10^{-12}$ W·m−2) in photon radiant flux density occurred when there were marked deviations from random variations suggesting that the correlative variable for intent was coupled to cerebral photon emission. In some other embodiments, cross-spectral analyses indicated a significant coupling between photon density and deviation from random variation. In some other embodiments, there may be a moderately strong correlation between the strength of coherence between the deviations during intention, and photon emission and entropy within the temporal distribution of the "random" number variations, and may suggest a strong relationship between intentions and BPEs.

In some other embodiments, emission of light particles (biophotons) may seem to be the mechanism through which an intention produces its effects. In some other embodiments, living organisms may emit a constant current of photons as a mean to direct instantaneous nonlocal signals from one part of the body to another and to the outside world. In some other embodiments, direct intention manifests itself as an electric and magnetic energy producing an ordered flux of photons. In yet some other embodiments, intentions may seem to operate as highly coherent frequencies capable of changing the molecular structure of matter.

In some embodiments, BPE may display a rather reliable and sensitive fingerprint of a living system, a noninvasive measurements of the spectral intensities provide a powerful tool for identifying biological systems as well as for characterizing their response to external influences. In some other embodiments, bio-indication by means of BPE (and/or delayed luminescence) may probably be the most sensitive test for examining the influence of external factors.

In one embodiment, equipment used to measure bio-emissions are special devices, for example, photomultiplier tubes or CCD cameras. In a further embodiment, thermoelectric cooler may be used to cool the photomultiplier tube to negative 26 degrees centigrade. This is done to reduce interference from the electrical devices.

Figure 4:
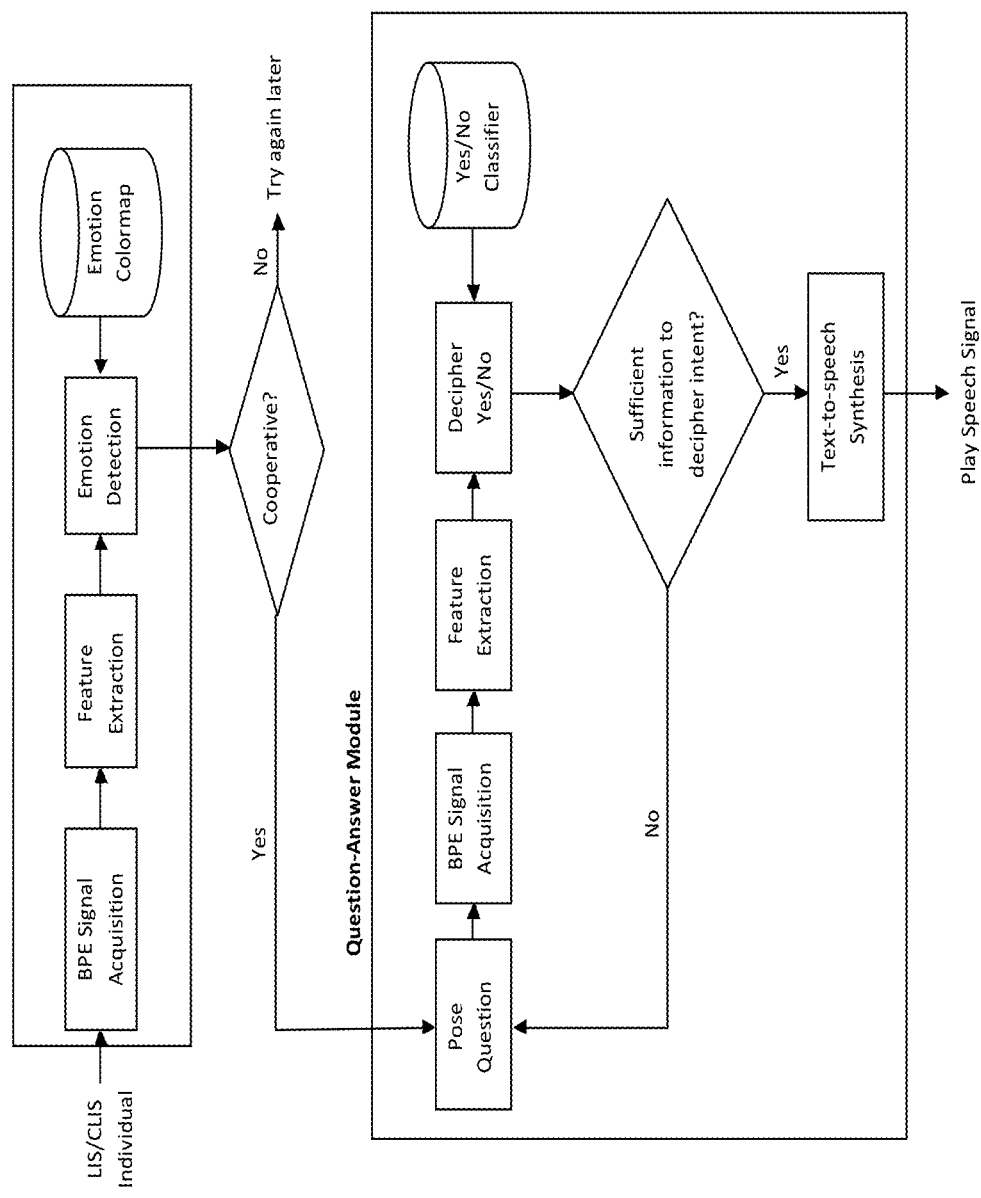
FIG. 4 illustrates an exemplary block diagram describing the functionality of the proposed Thought To Speech (TTS) system.

In accordance with the present invention, the system analyses the BPE signal generated as a result of thought associated with a stimulus, e.g., a question or an event. FIG. 4 illustrates an exemplary block diagram describing the functionality of the proposed Thought-to-Speech (TTS) system. The system includes a recognition module and a question-answer module. First, the LIS/CLIS patient is connected to the system to be monitored. Biophoton signals that are emitted from the LIS/CLIS patient are first acquired. From the acquired signal, a set of features are extracted. In one embodiment, extraction of the features may be done manually or the system may be programmed to automatically extract these features. The features extracted from the signals are compared with a repository, which for example contains emotional colourmap, and specific emotions may be detected. From the emotion detected, it can be ascertained whether the patient is in a cooperative state or a non-cooperative state. If the patient is in a non-cooperative state, the process is repeated again until it can be determined that the patient is in a cooperative state. If the patient is in a cooperative then the process goes to the question-answer module.

In the question-answer module, when the patient is in the cooperative state, first a question is posed to the patient. After a question is posed to the patient, biophotons emitted from the patient are collected/recorded, wherein the biophoton emission may contain an answer in binary form to the question posed to the patient. From the signal (also referred to as biophoton or biophoton emission), features, the signal is processed to extract features. From the features extracted, it should be deciphered whether the answer to the question posed to the patient is a YES or a NO. The extracted feature may be further interfaced with a classifier, such as a repository, containing such answers. The question posed are typically related to a status of the patient, such as an emotional status or an intent of the patient. If there is sufficient information to decipher the intent of the patient, the information is passed to a text-to-speech synthesizer and the intent is output by playing the speech signal. If there is insufficient information to decipher the person's intent, then the process is repeated by repeating the question and the intent of the patient can be deciphered.

In one embodiment, knowing an emotional state of mind of an individual may have other benefits too. In an example embodiment, it would help in choosing an appropriate set of questions and a manner of presenting questions in the following step. In a further embodiment, by continuously monitoring a patient and identifying a psychological state of a person a system could possibly generate a behavior pattern. In a further embodiment, this could help identifying situations when a person is likely to experience emotions such as pain, anger, fear, compassion, etc. In a further embodiment, based on these observations a suitable patient management system may be designed, as communicating emotional state of joy, pain, etc., to an environment may significantly improve the quality of life of the LIS and CLIS patients.

In one embodiment, the question answer step works as follows, first, the system engages a subject (person/patient/living object) in a conversation. In a further embodiment, it poses questions that have binary answers (YES/NO) to the subject. In a further embodiment, it identifies an actual answer provided in a response. In a further embodiment, BPE patterns are again recorded and classified to detect the type of intension: positive (Yes) or negative (No). In an example embodiment, the system might ask a question, "Are you hungry?" and read the response by decoding the BPE patterns emitted by the person's brain as a radiation (reaction). In a further embodiment, other parts of the patient may also emit such biophotons such as the fingers, palms, chest etc., and these signals may be collected and processed in accordance with the embodiments of the present disclosure. In a further embodiment, the system may go one step further to decipher whether the person is 'mildly hungry' or 'very hungry' by observing the characteristics of the emissions generated, for example, the intensity of the emissions. In a further embodiment, it may next go on asking related questions such as, "Do you want to eat chapatti?", "Do you want to eat chapatti with curry?" and so on. In a further embodiment, at the end of all these related question/answer session, the system would be able to generate sentences which will speak what the patient intends to communicate. In an example embodiment, for instance, "I am very hungry. I would like to have a chapatti with curry".

It should be noted that the embodiments of the present disclosure may be implemented through hardware, software or a combination of software and hardware. The hardware part may be implemented by a specific logic; the software part may be stored in a memory and executed by a proper instruction execution system, e.g., a micro-processor or specifically designed hardware. Those skilled in the art may understand that the above apparatus and method may be implemented by a computer executable instruction or by being included in processor control code, e.g., such code is provided on a programmable memory or a data carrier such as an optical or electronic signal carrier.

Figure 5:
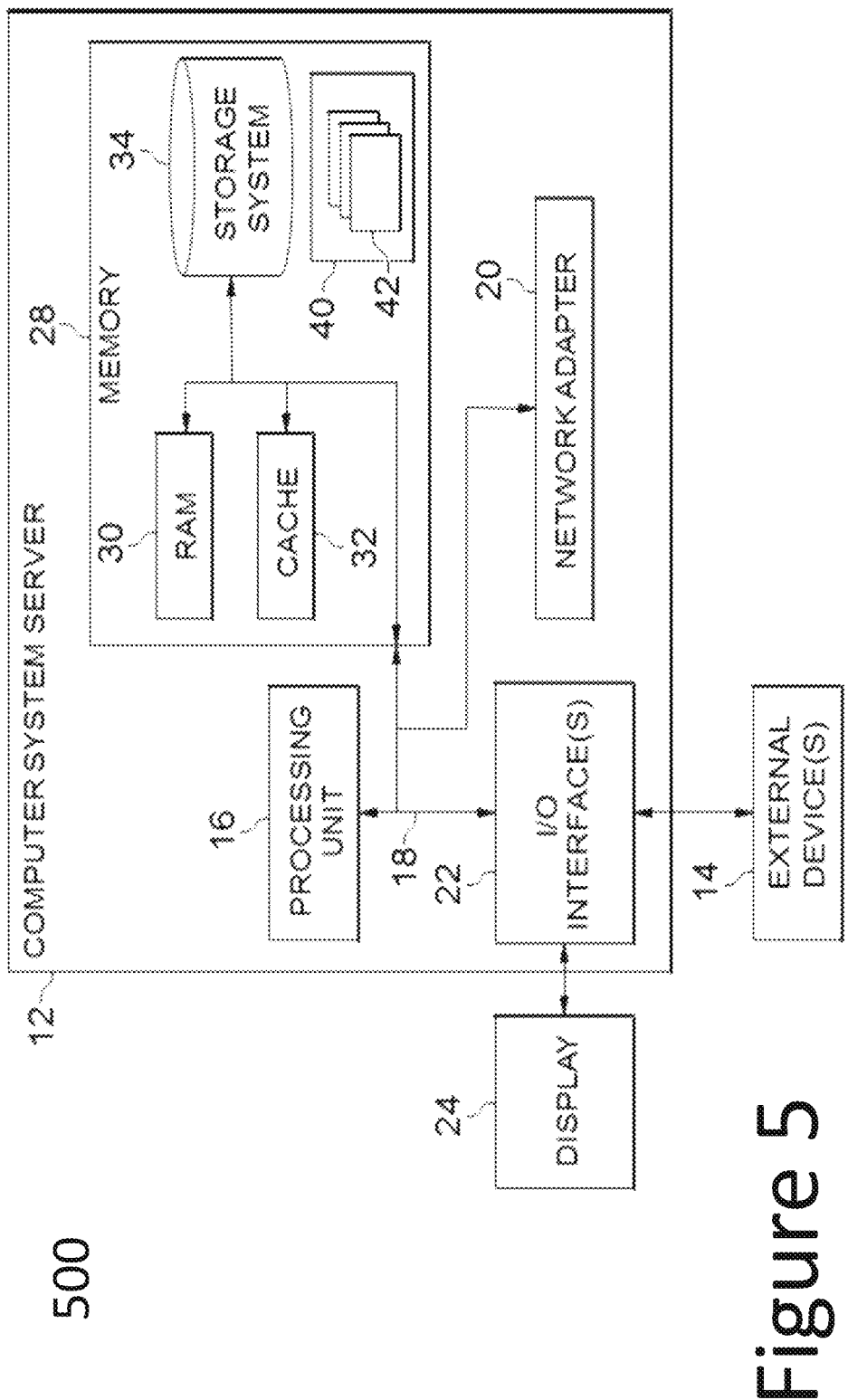
FIG. 5 illustrates an exemplary computer system on which the method may be implemented.

FIG. 5 shows a block diagram of an exemplary computer system/server 12 which is applicable to implement the embodiments of the present invention. Computer system/server 12 shown in FIG. 5 is only illustrative and is not intended to suggest any limitation as to the scope of use or functionality of embodiments of the invention described herein.

As shown in FIG. 5, computer system/server 12 is shown in the form of a general-purpose computing device. The components of computer system/server 12 may include, but are not limited to, one or more processors or processing units 16, system memory 28, and bus 18 that couples various system components (including system memory 28 and processor 16).

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the disclosure.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 6:
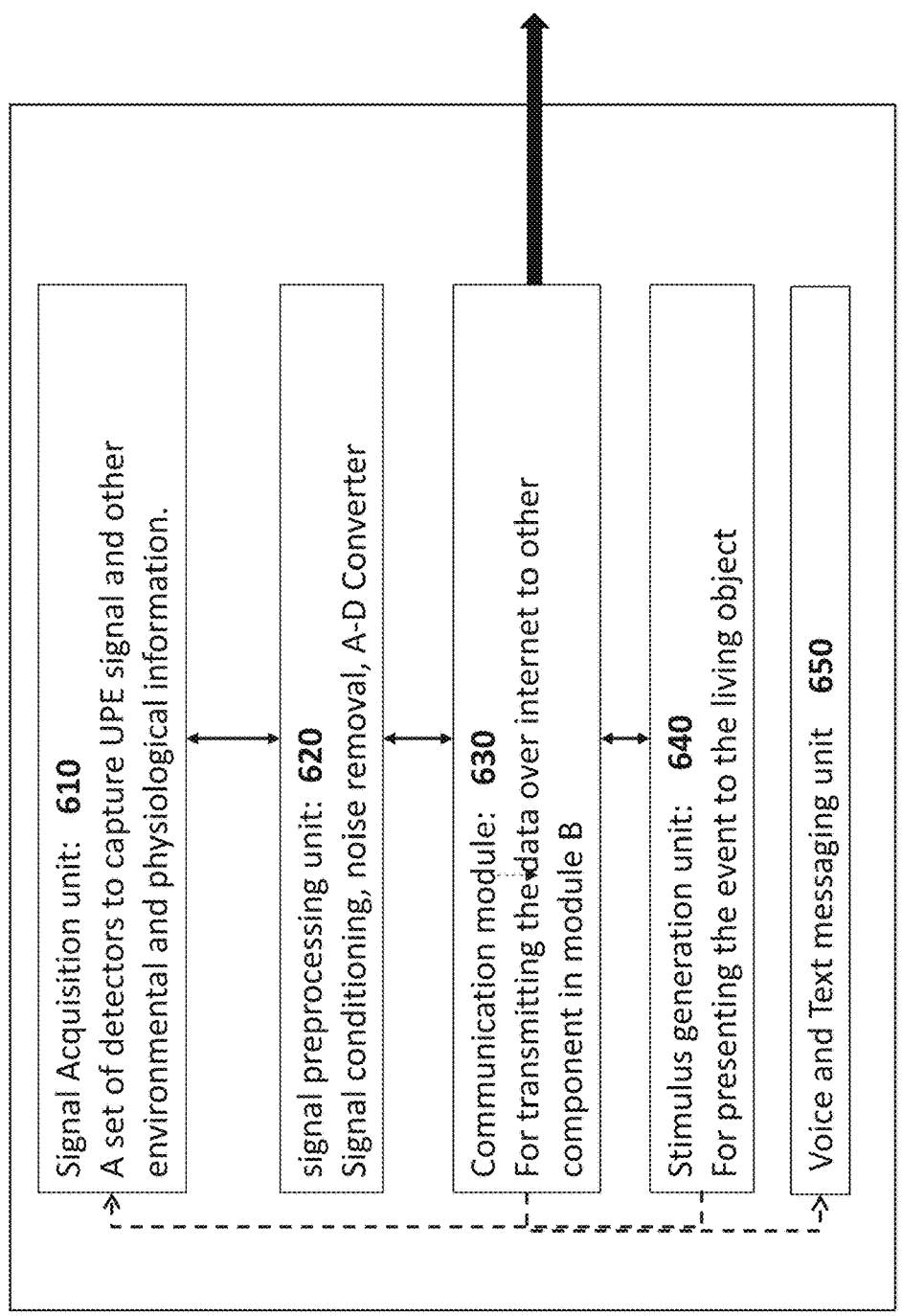
FIG. 6 illustrates an exemplary embodiment of the processing unit in accordance with the present disclosure.

FIG. 6 illustrates an exemplary embodiment of the functionality of processing a signal in accordance with the present disclosure Signal acquisition unit 610 includes a set of detectors to capture UPE/BPE signal and other environmental and physiological information. For example, in some embodiment photodetectors, CCD cameras etc., may be used to capture such BPE signals. Signal acquisition unit 610 passes the acquired/collected signal to signal preprocessing unit 620, which is configured for signal conditioning, noise removal and then converting an analog signal to a digital signal. Communication module 630 is couple to signal preprocessing module and is configured for transmitting the data over internet to other components and processing the data. Stimulus generation module 640 is coupled to the system and configured for presenting an event to the living object. Voice and text messaging module 650 is coupled to the other modules and is configured to output the emotions/stimulus from the living object to a third party in a commutable manner, for example the question and a relevant answer may be output.

In particular, according to embodiments of the present invention, the process as described above with reference to FIGS. 1-4 may be implemented as a computer software program. For example, embodiments of the present disclosure include a computer program product, which includes a computer program tangibly embodied on the machine-readable medium. The computer program includes program code for performing methods as disclosed above.

Generally, various exemplary embodiments of the present disclosure may be implemented in hardware or application-specific circuit, software, logic, or in any combination thereof. Some aspects may be implemented in hardware, while other aspects may be implemented in firmware or software executed by a controller, a microprocessor or other computing device. When various aspects of the embodiments of the present disclosure are illustrated or described into block diagrams, flow charts, or other graphical representations, it would be understood that the blocks, apparatus, system, technique or method described here may be implemented, as non-restrictive examples, in hardware, software, firmware, dedicated circuit or logic, common hardware or controller or other computing device, or some combinations thereof.

Besides, each block in the flowchart may be regarded as a method step and/or an operation generated by operating computer program code, and/or understood as a plurality of coupled logic circuit elements performing relevant functions. For example, embodiments of the present disclosure include a computer program product that includes a computer program tangibly embodied on a machine-readable medium, which computer program includes program code configured to implement the method described above.

In the context of the present disclosure, the machine-readable medium may be any tangible medium including or storing a program for or about an instruction executing system, apparatus or device. The machine-readable medium may be a machine-readable signal medium or machine-readable storage medium. The machine-readable medium may include, but not limited to, electronic, magnetic, optical, electro-magnetic, infrared, or semiconductor system, apparatus or device, or any appropriate combination thereof. More detailed examples of the machine-readable storage medium include, an electrical connection having one or more wires, a portable computer magnetic disk, hard drive, random-access memory (RAM), read-only memory (ROM), erasable programmable read-only memory (EPROM or flash memory), optical storage device, magnetic storage device, or any appropriate combination thereof.

The computer program code for implementing the method of the present invention may be written with one or more programming languages. These computer program codes may be provided to a general-purpose computer, a dedicated computer or a processor of other programmable data processing apparatus, such that when the program codes are executed by the computer or other programmable data processing apparatus, the functions/operations prescribed in the flowchart and/or block diagram are caused to be implemented. The program code may be executed completely on a computer, partially on a computer, partially on a computer as an independent software packet and partially on a remote computer, or completely on a remote computer or server.

Besides, although operations are depicted in a particular sequence, it should not be understood that such operations are completed in a particular sequence as shown or in a successive sequence, or all shown operations are executed so as to achieve a desired result. In some cases, multi-task or parallel-processing would be advantageous. Likewise, although the above discussion includes some specific implementation details, they should not be explained as limiting the scope of any invention or claims, but should be explained as a description for a particular embodiment of a particular disclosure. In the present specification, some features described in the context of separate embodiments may also be integrated into a single embodiment. On the contrary, various features described in the context of a single embodiment may also be separately implemented in a plurality of embodiments or in any suitable sub-group.

Various amendments and alterations to the exemplary embodiments of the present disclosure as above described would become apparent to a person skilled in the relevant art when viewing the above description in connection with the drawings. Any and all amendments still fall within the scope of the non-limiting exemplary embodiments of the present disclosure. Besides, the above description and drawings offer an advantage of teaching, such that technicians relating to the technical field of these embodiments of the present disclosure would envisage other embodiments of the present disclosure as expounded here.

Although the operations of the method according to the embodiments of the present disclosure are described in a specific order in the drawings, it does not require or imply that these operations have to be performed in that specific order, or a desired result can only be achieved by performing all of the illustrated operations. On the contrary, the steps illustrated in the flow diagrams may change their execution order. Additionally or alternatively, some steps may be omitted, a plurality of steps may be combined into one step for execution, and/or one step may be decomposed into a plurality of steps for execution. It should also be noted that the features and functions of two or more modules according to the embodiments of the present disclosure may be embodied in one module. In turn, features and functions of one module described above may also be further divided into a plurality of modules for embodiment.

Although the present disclosure has been described with reference to several preferred embodiments, it should be understood that the present disclosure is not limited to the preferred embodiments disclosed here. Embodiments of the present disclosure intend to cover various modifications and equivalent arrangements within the spirit and scope of the appended claims.

This disclosure has been presented for purposes of illustration and description but is not intended to be exhaustive or limiting. Many modifications and variations will be apparent to those of ordinary skill in the art. The embodiments were chosen and described in order to explain principles and practical application, and to enable others of ordinary skill in the art to understand the disclosure.

Although illustrative embodiments of the invention have been described herein with reference to the accompanying drawings, it is to be understood that the embodiments of the invention are not limited to those precise embodiments, and that various other changes and modifications may be affected therein by one skilled in the art without departing from the scope or spirit of the disclosure.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C-+ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method for communicating with a living object, comprising:
   collecting, at an information handling device, at least one biophoton signal received from a living object, in response to an event posed to the living object, wherein the living object is in a communicative state via the at least one biophoton signal with a person talking to the living object, wherein the at least one biophoton signal spontaneously emits from the living object and comprises a ultraweak biophoton emission triggered by the event, wherein the living object is in a locked-in state;
   extracting, using a processor, a set of pre-determined features from the biophoton signal collected, wherein the set of pre-determined features relate to an intent of the living object in response to the event; and
   determining, responsive to extracting, the intent associated with the living object in responsive to the event posed to the living object from the biophoton signal, wherein the information handling device comprises a text-to-speech system, wherein the text-to-speech system is configured to respond to the event by outputting the intent as a speech signal.

2. The method of claim 1, wherein the biophoton signal is a low intensity photon.

3. The method of claim 1, wherein the event is at least one action by the person to communicate with the living object.

4. The method of claim 1, wherein the communicative state of the living object comprises a cooperative state determined from an emotion detected from the biophoton signal to the living object.

5. The method of claim 1, wherein the communicative state of the living object comprises a non-cooperative state, based upon checking after a period of time if there is a change in the cooperative state of the living object.

6. The method of claim 1, further comprising collecting and analyzing the biophoton signal emitted in response to the event.

7. The method of claim 1, wherein the biophoton signal is a wavelength range of 200 nm to 800 nm.

8. The method of claim 1, wherein the response to the event posed to the living object is a binary response.

9. The method of claim 1, further comprising at least one detector configured to monitor a living object.

10. An information handling device, comprising:
    a processor;
    a memory device that stores instructions executable by the processor to:
    collect, at an information handling device, at least one biophoton signal received from a living object, in response to an event posed to the living object, wherein the living object is in a communicative state via the at least one biophoton signal with a person talking to the living object, wherein the at least one biophoton signal spontaneously emits from the living object and comprises a ultraweak biophoton emission triggered by the event, wherein the living object is in a locked-in state;
    extract, using a processor, a set of pre-determined features from the biophoton signal collected, wherein the set of pre-determined features relate to an intent of the living object in response to the event; and
    determine, responsive to extracting, the intent associated with the living object responsive to the event posed to the living object from the biophoton signal, wherein the information handling device comprises a text-to-speech system, wherein the text-to-speech system is configured to respond to the event by outputting the intent as a speech signal.

11. The information handling device of claim 10, wherein the biophoton signal is a low intensity photon.

12. The information handling device of claim 10, wherein the event is at least one action by the person to communicate with the living object.

13. The information handling device of claim 10, wherein the communicative state of the living object comprises a cooperative state determined from an emotion detected from the biophoton signal to the living object.

14. The information handling device of claim 10, wherein the communicative state of the living object comprises a non-cooperative state, based upon checking after a period of time if there is a change in the cooperative state of the living object.

15. The information handling device of claim 10, further comprising collecting and analyzing the biophoton signal emitted in response to the event.

16. The information handling device of claim 10, wherein the biophoton signal is a wavelength range of 200 nm to 800 nm.

17. The information handling device of claim 10, wherein the response to the event posed to the living object is a binary response.

18. A product, comprising:
    a storage device that stores code, the code being executable by a processor and comprising:
    code that collects, at an information handling device, at least one biophoton signal received from a living object, in response to an event posed to the living object, wherein the living object is in a communicative state via the at least one biophoton signal with a person talking to the living object, wherein the at least one biophoton signal spontaneously emits from the living object and comprises a ultraweak biophoton emission triggered by the event, wherein the living object is in a locked-in state;
    code that extracts, using a processor, a set of pre-determined features from the biophoton signal collected, wherein the set of pre-determined features relate to an intent of the living object in response to the event; and
code that determines, responsive to extracting, the intent associated with the living object responsive to the event posed to the living object from the biophoton signal, wherein the information handling device comprises a text-to-speech system, wherein the text-to-speech system is configured to respond to the event by outputting the intent as a speech signal.

\* \* \* \* \*